United States Patent [19]

Cochran et al.

[11] 4,398,041

[45] Aug. 9, 1983

[54] PROCESS FOR MANUFACTURING ALKYLAMINES

[75] Inventors: Robert N. Cochran, West Chester; Michel Deeba, Emmaus, both of Pa.

[73] Assignee: Air Products and Chemicals, Inc., Allentown, Pa.

[21] Appl. No.: 344,246

[22] Filed: Jan. 29, 1982

[51] Int. Cl.$^3$ .............................................. C07C 85/06
[52] U.S. Cl. ................................... 564/479; 564/497; 564/499
[58] Field of Search ........................ 564/479, 480, 478

[56] References Cited

U.S. PATENT DOCUMENTS

| | | | |
|---|---|---|---|
| 3,384,667 | 5/1968 | Hamilton | 260/585 |
| 4,191,709 | 3/1980 | Parker et al. | 564/479 |
| 4,205,012 | 5/1980 | Parker et al. | 564/479 |
| 4,217,240 | 8/1980 | Bergna | 564/479 X |
| 4,229,374 | 10/1980 | Slaugh et al. | 260/563 |
| 4,254,061 | 3/1981 | Wiegert | 564/479 |

Primary Examiner—John Doll
Attorney, Agent, or Firm—Michael Leach; E. Eugene Innis; James C. Simmons

[57] ABSTRACT

A process for converting a $C_1$–$C_4$ alcohol to a non-equilibrium controlled distribution of mono-, di- and trialkylamines is disclosed. A mixture of the alcohol and ammonia is reacted in a first conversion reactor containing a shape selective catalyst to yield a first product stream comprising the mono- and disubstituted alkylamines and substantially no trisubstituted alkylamine. A predetermined fraction of the first product stream is removed and the remainder of the stream is reacted in a second conversion reactor containing a catalyst which yields a second product stream comprising an equilibrium controlled distribution of the mono-, di- and trisubstituted alkylamine. The fraction of the first product stream and the second product stream are combined to yield an alkylamines stream comprising a non-equilibrium controlled alkylamines distribution.

5 Claims, 1 Drawing Figure

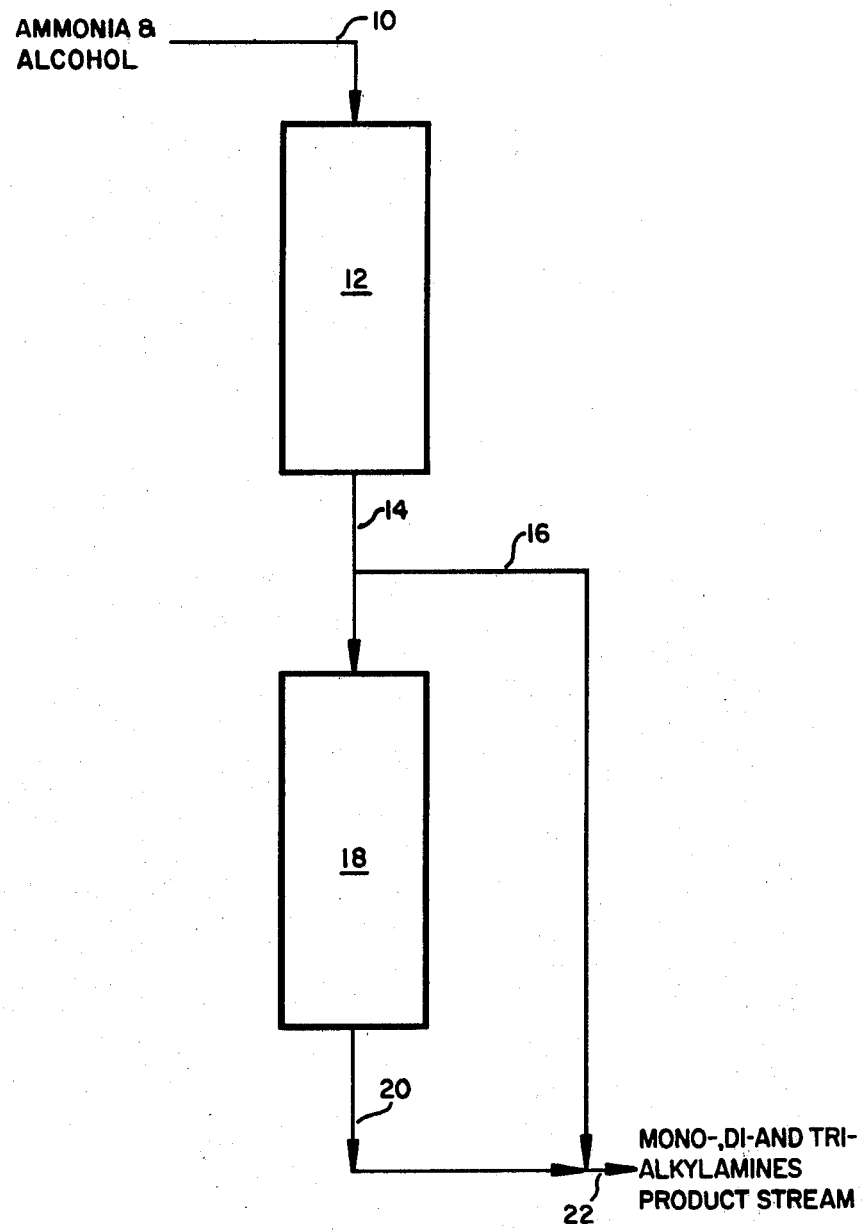

PROCESS FOR MANUFACTURING ALKYLAMINES

TECHNICAL FIELD

This invention relates to the preparation of alkylamines by a catalytic reaction between an alcohol and ammonia.

BACKGROUND OF THE INVENTION

Current process schemes for producing alkylamines from alcohols or their corresponding ethers require separation and recycling of certain of the amine products to obtain the desired alkylamines product distribution. For example, when using an amorphous silica-alumina catalyst for the production of the mono-, di- and trisubstituted methylamines from methanol and ammonia, such recycling is necessary because the product distribution of the methylamines is controlled by the rapid equilibria of the amines among themselves and ammonia.

The following reaction equations (1–3) show the production of the mono-, di- and trialkylamines from the starting materials comprising the alkanol (ROH) and ammonia:

$$ROH + NH_3 \rightarrow RNH_2 + H_2O \quad (1)$$

$$ROH + RNH_2 \rightarrow R_2NH + H_2O \quad (2)$$

$$ROH + R_2NH \rightarrow R_3N + H_2O \quad (3)$$

In addition to the above pathways for the three alkylamine products, the following equilibrium reaction equations (4–6) show another mechanism responsible for the alkylamines product distribution:

$$R_2NH + NH_3 \rightleftharpoons 2RNH_2 \quad (4)$$

$$R_3N + NH_3 \rightleftharpoons R_2NH + RNH_2 \quad (5)$$

$$R_3N + RNH_2 \rightleftharpoons 2R_2NH \quad (6)$$

At each set of conversion conditions comprising temperature, pressure, catalyst, ammonia:alcohol feed ratio and flow rate, the above reaction equations 1–6, particularly equilibrium reaction equations 4–6, necessarily yield an equilibrium controlled distribution of the mono-, di- and trialkylamines.

For example, with respect to the production of the methylamines from methanol and ammonia under given conversion conditions, these equilibria limit the amount of each methylamine in the product stream. Therefore, if the desired amine product is dimethylamine, the mono- and trisubstituted products typically are separated from the product stream and recycled to the reaction zone along with the excess ammonia to produce more dimethylamine from these less desired amines via the equilibrium reactions 4–6. However, the product stream will still comprise an equilibrium controlled methylamines product ratio. Such recycling of some of the amines product is required in amines processes whenever the composition of the desired product stream is other than the equilibria controlled distribution of the three amines.

One means for controlling the product distribution in a catalytic reaction between an alcohol and ammonia to produce alkylamines is disclosed in U.S. Pat. No. 3,384,667. This patent teaches a methed for producing monosubstituted and disubstituted amines in preference to trisubstituted amines by reacting ammonia with an alcohol in the presence of particular crystalline metal aluminosilicate catalysts. Such aluminosilicate catalysts have become known as shape selective catalysts.

U.S. Pat. No. 4,229,374 discloses a process for producing tertiary amines by reacting alcohols with ammonia, primary amines or secondary amines in the presence of a catalyst which comprises a mixture of copper, tin and an alkali metal supported on a suitable carrier.

U.S. Pat. No. 4,254,061 discloses a process for producing monomethylamine by reacting methanol and ammonia in such amounts so as to provide a C:N ratio, from the methanol and ammonia reactants, of 0.5–1.5 over a particular zeolite catalyst.

These prior art processes do not permit the production of a mono-, di- and trisubstituted alkylamine product stream in nonequilibrium controlled distribution. Furthermore, recycling of at least a portion of a less or undesired alkylamine is usually required in order to maximize the production of the desired alkylamines.

The amination reactions are exothermic. Thus, in an adiabatic plugged flow reactor for the production of methylamines, for example, the temperature rises by 150°–400° F. (66°–232° C.) depending on the ammonia:methanol feed ratio. The maximum allowable reactor temperature for methylamines is 800° F. (427° C.), above which thermal reactions yielding coke and cracked by-products make the process inoperative.

The present silica-alumina catalysts require feed temperatures above 600° F. (316° C.) to obtain commercial methylamines production requirements. With a starting temperature of 600° F. (316° C.), the molar feed ratio of ammonia-methanol must be higher than 2 for the maximum temperature in an adiabatic reactor to be less than 800° F. (427° C.). Therefore, greater than two-fold excess ammonia over the stoichiometric requirement must be used to avoid coking and cracking. Use of such excess ammonia means large ammonia separation stills to recycle the ammonia.

SUMMARY OF THE INVENTION

The invention provides a process for converting a $C_1$–$C_4$ alcohol to a predetermined nonequilibrium controlled distribution of the mono-, di- and trialkylamines without recycling a portion of the alkylamines product stream to the conversion reactor. The process comprises (a) passing a mixture of the $C_1$–$C_4$ alcohol and ammonia into a first conversion zone containing a shape selective crystalline aluminosilicate zeolite catalyst which has intracrystalline pores of diameter that pass the monosubstituted and disubstituted alkylamine products but are too small to pass the trisubstituted alkylamine product, (b) substantially completely converting the alcohol under conversion conditions to yield a first product stream comprising the mono- and disubstituted alkylamines while substantially suppressing the production of the trisubstituted alkylamine, (c) removing a predetermined fraction of the first product stream, (d) passing the remainder of the first product stream into a second conversion zone containing a catalyst which has intracrystalline pores sufficiently large to readily permit the production of an equilibrium controlled distribution of mono-, di- and trisubstituted alkylamines, (e) converting the mono- and disubstituted alkylamines of the first product stream in the second conversion zone under conversion conditions to yield a second product stream comprising an equilibrium controlled distribution of mono-, di- and trisubstituted alkylamines, and (f) combining the fraction of the first product stream from step (c) with the second product stream to yield a nonequilibrium controlled mono-, di- and trisubstituted alkylamine distribution.

The invention advantageously produces an alkylamines product stream containing mono- and dialkylamines in excess of an equilibrium controlled distribution. Thus, the usually more desirable mono- and dialkylamines can be obtained in greater quantities while still producing the trialkylamine without the recycling of alkylamine product to the conversion reactor.

As another advantage of the invention as it pertains to methylamines production, only a minimum excess of ammonia over the stoichiometric ammonia requirement is needed to form the methylamines and, accordingly, ammonia separation apparatus may be reduced in size and lower feed temperatures used.

DESCRIPTION OF THE DRAWINGS

The sole FIGURE is a flow diagram of the process of the invention.

DETAILED DESCRIPTION OF THE INVENTION

In accordance with the present invention the compound reacted with ammonia to produce the alkylamines is an alcohol of the general formula ROH, wherein R is an alkyl radical, straight or branched, having from 1 to 4 carbons atoms. Exemplary alcohols are methanol, ethanol, the propanols and the butanols, with methanol being the preferred alcohol for practicing the invention.

Contemplated as the functional, or operative, equivalents of the $C_1$–$C_4$ alcohols used in practicing the process of this invention are the corresponding ether derivatives. Accordingly, the preferred ether for reaction with ammonia is dimethyl ether.

Alkylamines which can be produced by the process in a predetermined nonequilibrium controlled monosubstituted:disubstituted:trisubstituted alkylamine ratio include, for example, the methylamines, the ethylamines, the n-propylamines, the i-propylamines, and the n-butylamines.

Referring to the sole FIGURE, a preheated mixture of ammonia and a $C_1$–$C_4$ alcohol is passed by line 10 into a first conversion reactor 12 which contains a shape selective zeolite catalyst having intracrystalline pores of a diameter that pass or absorb the monosubstituted and disubstituted alkylamine products but are too small to pass the trisubstituted alkylamine products. Essentially, the zeolite catalyst allows for the selective conversion of the alcohol and ammonia into mono- and dialkylamines while substantially supressing the production of trialkylamine. Exemplary shape selective crystalline aluminosilicate catalysts which have pores of a size to selectively yield primary and secondary amines for use as the catalyst bed in first conversion reactor are those crystalline aluminosilicates taught in U.S. Pat. No. 3,384,667 which is incorporated by reference. Suitable shape selective crystalline aluminosilicates for use in the process of this invention are H-erionite, 5A zeolite and macroporous H-chabazite-erionite, depending on reactor temperatures. For the production of methylamines, H-erionite is the catalyst of choice because it remains selective toward the mono- and dimethylamines even at temperatures above 700° F. The alcohol and ammonia are retained in the first conversion reactor under conversion conditions sufficient to aminate substantially all the alcohol.

A product stream essentially comprising mono- and dialkylamines, excess ammonia and water exit reactor 12 by line 14. A precalculated fraction of the product stream in line 14 is removed by line 16. The remainder of the product stream 14 containing a predetermined amount of mono- and disubstituted material for reforming into an equilibrium controlled distribution of the three alkylamines passes into the second conversion reactor 18.

The catalyst contained in second conversion reactor 18 may be any catalyst known in the art for effecting a conversion of a $C_1$–$C_4$ alcohol and ammonia to the mono-, di- and trisubstituted alkylamines in an equilibrium controlled distribution, such as the widely used silica-alumina catalyst. However, in a preferred embodiment for the production of a predetermined ratio of methylamines, certain crystalline aluminosilicate zeolite catalysts having enhanced activity, described in more detail below, are used in the reactor 18.

Under the conversion conditions existing in the second conversion reactor 18, the mono- and disubstituted alkylamines from first conversion reactor 12 are reformed according to the equilibrium reactions into an equilibrium controlled distribution of mono-, di- and trialkylsubstituted amines. Since preselected quantities of the mono- and disubstituted product were permitted to flow into the reactor operating under known conversion conditions, a predetermined equilibrium ratio of the three alkylamine products exits reactor 18 by line 20. The product stream fraction containing the mono- and disubstituted alkylamines in line 16 is combined with the product stream in line 20 to provide a final alkylamine product stream 22 containing the desired ratio of monoalkylamine:dialkylamine:trialkylamine which is at a nonequilibrium controlled distribution.

The final alkylamine product stream 22 is processed in an ammonia column of a separation train, not shown, where ammonia is first separated from the alkylamines which are then separated from each other, if necessary. The ammonia is then recycled.

However, it may be advantageous to pass each of the product streams in lines 16 and 20 through a separation train in order to separate the monomethylamine and dimethylamine of the first product stream and the monomethylamine, dimethylamine and trimethylamine of the second product stream. The same amines from each separator train are then combined. The advantage resides in the trimethylamine separation being an extractive step, requiring addition of water which is subsequently removed in a dehydration column. An energy savings could be realized since the water extraction and dehydration steps would not involve the total product distribution.

Generally, the mole ratio of ammonia to alcohol in the feed stream may range from about 0.5:1 to 6:1, and for the amination of methanol ranges preferably from about 1.5:1 to 2.5:1. Of course, the actual ammonia:alcohol molar ratio used depends on several factors including the desired final product distribution, the catalysts used in each of the two conversion reactors, the reaction temperatures and pressures existing in the conversion reactors and the fraction of the mono- and disubstituted product stream which is passed into the second conversion reactor.

The reaction temperatures used in the conversion reactors may range from about 250° to 425° C., and preferably from about 280° to 400° C. If the temperature is too low, the conversion of the alcohol and ammonia to mono- and disubstituted amines in the first conversion reactor and their subsequent reformation to the mono-, di- and trisubstituted amines in the second conversion reactor will be low requiring excessive contact times or, equivalently, low flow rates. If the temperature is too high, hydrocarbon by-product formation and catalyst coking becomes a significant problem.

The pressure utilized in the conversion reactors for carrying out the reaction is a pressure between about 1 to 50 atm with a pressure range of about 10 to 30 atm being preferred. In general, flow rates (GHSV) of about 1,000 to 30,000 ml of alcohol/cc of catalyst/hour, preferably 5,000 to 15,000 ml/cc/hour, may be used. When the desired amines product stream comprises the methylamines, as in the preferred embodiment of the invention, the preferred catalysts for each of the conversion reactors is one possessing superior methanol conversion rates selected from macroporous H-chabazite-erionite, REY zeolite, H-Y zeolite, H-erionite, 5A zeolite and H-mordenite. The anticipated reactor temperatures may determine the particular catalyst used in each reactor. Those catalysts from this group of highly acidic aluminosilicate catalysts which are also shape selective are used in the first reactor.

The following Examples 1-7 illustrate the superior methanol conversion rates for the preferred catalysts for use in the first and second conversion reactors. The term "methanol conversion rate" means the rate at which methanol is converted to methylamines per gram of catalyst as expressed by the equation:

$$\text{Rate} = \frac{g - \text{mole (MMA} + 2\text{DMA} + 3\text{TMA})}{g - \text{catalyst} - \text{second}}$$

where MMA=monomethylamine, DMA=dimethylamine and TMA=trimethylamine.

EXAMPLES 1-7

A series of runs 1-7 were made to produce methylamines. Ammonia and methanol in such amounts so as to provide an ammonia:methanol molar ratio of about 2:1 were passed over about 5.34 grams of catalyst in a Berty recycle reactor which is a fixed bed reactor with a large (greater than 20) internal recycle ratio. Under these conditions the Berty reactor is gradientless and behaves like a continually stirred torque reactor (CSTR). Rates of reaction can be calculated directly as moles converted per gram of catalyst per second of residence time.

The reaction was performed at a total pressure of 18 atm at a gas hourly space velocity (GHSV) of 9,300 and at a variety of temperatures from 550° to 750° F. (288° to 399° ). The reactor feeds and effluent were analyzed by an on-line calibrated gas chromatograph. The streams were maintained gaseous from the reactor to the chromatograph sampling valve.

The catalysts tested were amorphous silica-alumina, H-mordenite, 5A zeolite, REY zeolite, H-Y zeolite, macroporous H-chabazite-erionite and H-erionite.

The amorphous silica-alumina was a Ketjen LA-30 catalyst. The 5A zeolite was a calcium cation exchanged sodium A zeolite. The REY zeolite was Union-Carbide's SK-500 rare earth exchanged zeolite catalyst.

The macroporous H-chabazite-erionite catalyst was prepared from 3 kg of Anaconda 5050F (chabazite-erionite) powder which was exchanged three times using 10% aqueous ammonium nitrate (5 l) for each exchange and reslurrying after each filtration. The material was washed three times on the filter using 5 l deionized water each time and then dried at 250° F. (121° C.) without air circulation. The dried, ammonium exchanged material (300 g) was mixed thoroughly with cornstarch (6 g) for 30 minutes and $\frac{1}{8}$ inch diameter $\times \frac{1}{8}$ inch length (32 mm $\times$ 32 mm) pellets were prepared. The pellets were heat treated at 1,000° F. (538° C.) for two hours in flowing air saturated with 10% ammonium hydroxide solution and two hours in dry air.

The remaining hydrogen exchanged aluminosilicate catalysts, namely H-Y zeolite, H-erionite, and H-mordenite were prepared from Na Y zeolite, erionite ore, and sodium mordenite, respectively, by ion exchange with aqueous ammonium chloride followed by calcining at 400° C.

Table I sets forth the methanol conversion rates in terms of gram-mole methanol/grams catalyst-second for the catalyst tested at the designated temperatures.

Table II shows the methylamines product split in the reactor effluent stream. The mole %'s of monomethylamine (MMA), dimethylamine (DMA) and trimethylamine (TMA) were calculated based on the areas under the chromatogram curves for each amine with response factors determined using measured blends of the amines.

TABLE I

METHANOL CONVERSION RATES
(g mol CH$_3$OH/g cat sec)

| CATALYST | 550° F. (288° C.) | 600° F. (316° C.) | 650° F. (343° C.) | 700° F. (371° C.) | 750° F. (399° C.) |
| --- | --- | --- | --- | --- | --- |
| 1 Silica-alumina | $5.0 \times 10^{-7}$ | $1.5 \times 10^{-6}$ | $5.2 \times 10^{-6}$ | $1.5 \times 10^{-5}$ | $3.7 \times 10^{-5}$ |
| 2 5A zeolite | $24.7 \times 10^{-7}$ | $5.4 \times 10^{-6}$ | $12.3 \times 10^{-6}$ | $2.0 \times 10^{-5}$ | — |
| 3 REY zeolite | $160 \times 10^{-7}$ | $29 \times 10^{-6}$ | $39 \times 10^{-6}$ | — | $7.3 \times 10^{-5}$ |
| 4 H—chabazite-erionite | $149 \times 10^{-7}$ | $26.5 \times 10^{-6}$ | $36.2 \times 10^{-6}$ | $5.4 \times 10^{-5}$ | $7.7 \times 10^{-5}$ |
| 5 H—erionite | $75 \times 10^{-7}$ | $14.3 \times 10^{-6}$ | $23.7 \times 10^{-6}$ | $3.4 \times 10^{-5}$ | $4.6 \times 10^{-5}$ |
| 6 H—mordenite | $67.5 \times 10^{-7}$ | $17.3 \times 10^{-6}$ | $24.5 \times 10^{-6}$ | $3.25 \times 10^{-5}$ | $3.8 \times 10^{-5}$ |
| 7 H—Y zeolite | $96.5 \times 10^{-7}$ | $23 \times 10^{-6}$ | $37 \times 10^{-6}$ | $5.1 \times 10^{-5}$ | $5.7 \times 10^{-5}$ |

TABLE II

COMPARISON OF METHYLAMINES PRODUCT SPLIT
(mole % MMA, mole % DMA, mole % TMA)

| CATALYST | TEMPERATURE | | | | |
|---|---|---|---|---|---|
| | 550° F. (288° C.) | 600° F. (316° C.) | 650° F. (343° C.) | 700° F. (371° C.) | 750° F. (399° C.) |
| 1 Silica-alumina | (59, 25, 15) | (35, 11, 43) | (31, 27, 42) | (33, 27, 40) | (34, 28, 37) |
| 2 5A zeolite | (82, 18, 0) | (70, 30, 0) | (56, 31, 13) | (38, 31, 31) | — |
| 3 REY zeolite | (26, 22, 53) | (21, 29, 50) | (23, 33, 44) | — | (31, 37, 32) |
| 4 H—chabazite-erionite | (69, 31, 0) | (54, 46, 0) | (48, 42, 10) | (47, 43, 11) | (46, 41, 13) |
| 5 H—erionite | (87, 13, 0) | (81, 19, 0) | (74, 26, 0) | (67, 33, 0) | (60, 34, 6) |
| 6 H—mordenite | (82, 18, 0) | (65, 22, 13) | (57, 25, 18) | (55, 26, 19) | (54, 25, 21) |
| 7 H—Y zeolite | (58, 20, 22) | (43, 38, 19) | (37, 42, 21) | (39, 39, 22) | (43, 34, 23) |

The 5A zeolite catalyst suffered from poor thermal stability at the higher temperatures which, it is believed, explains its approach to the behavior of amorphous silica-alumina at about 700° F. (371° C.) and the lack of data at 750° F. (399° C.).

As can be seen from the data in Table I, when compared to the commercially used amorphous silica-alumina, REY zeolite, H-Y zeolite, macroporous H-chabazite-erionite, H-erionite and H-mordenite exhibited superior methanol conversion rates in the temperature range from about 550° F. (288° C.) to about 750° F. (399° C.). At temperatures of about 600° F. (316° C.) or below, these particular catalysts afforded extraordinarily high methanol conversion rates.

However, Table II shows, especially at temperatures of about 600° F. (316° C.) or below, that 5A zeolite, macroporous H-chabazite-erionite, H-erionite and H-mordenite demonstrate shape selectivity in that little or no trimethylamine product was detected. Therefore, these particular crystalline aluminosilicates are useful as the catalyst for the first conversion reactor. Since 5A zeolite demonstrates instability at temperatures of about 700° F. (371° C.) or greater, macroporous H-chabazite-erionite, H-erionite and H-mordenite are preferred for the first reactor.

The catalyst in the second conversion reactor may be silica-alumina, H-Y zeolite or REY zeolite which showed the production of the mono-, di- and trisubstituted amines.

The quantity of excess ammonia to be recycled after separation from the methylamines product stream 22 in the FIGURE can be reduced in this process compared to conventional processes if the preferred catalysts are used. For example, the preferred acidic zeolite catalysts in the two reactors are substantially more active than conventional silica-alumina catalysts and allow commercial production rates to be achieved with lower feed temperatures. As the feed temperature is lowered, lower ammonia:methanol molar feed ratios can be used before maximum temperatures of 800° F. (427° C.) are reached. If a feed temperature of 450° F. (232° C.) is used with the more active catalysts instead of 600° F. (316° C.) with conventional silica-alumina, the ammonia:methanol feed ratio can be reduced from 2.5 to 1.0 for a maximum adiabatic reactor temperature of 800° F. (429° C.).

EXAMPLE 9

Again referring to the FIGURE, ammonia and methanol in a molar ratio (N:R) of 1.5:1.0, at a gas hourly space velocity of 1000, a feed temperature of 288° C. and a pressure of 18 atm is passed by line 10 into contact with a bed of H-erionite catalyst in first conversion adiabatic reactor 12. Under such conversion conditions, the methanol and ammonia react to produce a product stream in line 14 at an outlet temperature of 400° C. comprising 11.7 mole percent monomethylamine, 14.2 mole percent dimethylamine, 34.1 mole percent ammonia, 40.0 percent water and essentially no trimethylamine or methanol. The residence time is sufficient to ensure substantially complete amination of the methanol.

The product stream in line 14 is cooled at 288° C. and 80% of the stream is removed via line 16 before the remaining 20% enters the second conversion adiabatic reactor 18 containing REY zeolite catalyst at a pressure of 17.5 atm and a gas hourly space velocity of 1000. The fraction of product stream 14 which enters the second conversion reactor 18 is reformed to an equilibrium controlled distribution of monomethylamine, dimethylamine and trimethylamine in a molar ratio of 31:24:45 exiting as product stream 20.

The product stream leaving the second conversion reactor 18 in line 20 comprises 5.8 mole percent monomethylamine, 4.5 mole percent dimethylamine, 8.4 mole percent trimethylamine, 41.3 mole percent ammonia and 40.0 mole percent water and combines with the fraction of the product stream from the first conversion reactor in line 16 to afford a final alkylamines product stream 22 comprising a 42.4:48.6:9.0 molar ratio of monomethylamine:dimethylamine:trimethylamine.

STATEMENT OF INDUSTRIAL APPLICATION

The inventive process provides a method for producing a product stream containing mono-, di- and trialkylamines in a non-equilibrium controlled distribution in the catalytic conversion of an alcohol and ammonia. The process can be used to produce the commercially valuable methylamines which are employed in tanning and in organic synthesis to manufacture compounds such as surface active agents, fungicides and insecticides for agriculture.

We claim:

1. A process for converting a $C_1$-$C_4$ alcohol to a predetermined nonequilibrium controlled distribution of monosubstituted, disubstituted and trisubstituted alkylamines which comprises (a) passing a mixture of the $C_1$-$C_4$ alcohol and ammonia into a first conversion zone containing a shape selective crystalline aluminosilicate zeolite catalyst which has intracrystalline pores of a diameter that pass the monosubstituted and disubstituted alkylamine products but are too small to pass the trisubstituted alkylamine product, (b) substantially completely converting the alcohol under conversion conditions in the first conversion zone to yield a product stream comprising the monosubstituted and disubstituted alkylamines while substantially suppressing the production of the trisubstituted alkylamine, (c) removing a predetermined fraction of the first product stream, (d) passing the remainder of the first product stream into a second conversion zone containing a catalyst which has intracrystalline pores sufficiently large to readily permit the production of an equilibrium controlled distribution of monosubstituted, disubstituted and trisubstituted alkylamine, (e) converting the monosubstituted and disubstituted alkylamines of the first product stream under conversion conditions in the second conversion zone to yield a second product stream comprising an equilibrium controlled distribution of monosubstituted, disubstituted and trisubstituted alkylamines, and (f) combining the fraction of the first product steam from step (c) with the second product stream to yield a nonequilibrium controlled monosubstituted, disubstituted and trisubstituted alkylamine distribution.

2. The invention of claim 1 wherein the alcohol is methanol.

3. The invention of claim 2 wheren the catalyst in the first conversion zone is H-erionite or macroporous H-chabazite-erionite.

4. The invention of claims 2 or 3 wherein the catalyst in the second conversion zone is silica-alumina or REY zeolite.

5. The invention of claim 1 wherein the feed stream to the first conversion zone comprises ammonia and the $C_1$–$C_4$ alcohol in a molar ratio from about 0.5:1 to 6:1 at a pressure from about 1 to 50 atmospheres and a temperature from 250° to 425° C. flowing at a gas hourly space velocity of 1,000 to 30,000 ml of alcohol per cc of catalyst per hour.

* * * * *

UNITED STATES PATENT AND TRADEMARK OFFICE
CERTIFICATE OF CORRECTION

PATENT NO. : 4,398,041

DATED : August 9, 1983

INVENTOR(S) : Robert N. Cochran and Michel Deeba

It is certified that error appears in the above-identified patent and that said Letters Patent is hereby corrected as shown below:

Column 9, Line 16
 Delete "steam" and substitute therefor -- stream --

Signed and Sealed this

Tenth Day of July 1984

[SEAL]

Attest:

GERALD J. MOSSINGHOFF

Attesting Officer

Commissioner of Patents and Trademarks